US008338457B2

(12) United States Patent
Iadarola et al.

(10) Patent No.: US 8,338,457 B2
(45) Date of Patent: Dec. 25, 2012

(54) SELECTIVE ABLATION OF PAIN-SENSING NEURONS BY ADMINISTRATION OF A VANILLOID RECEPTOR AGONIST

(75) Inventors: Michael J. Iadarola, Washington, DC (US); Zoltan Olah, Kensington, MD (US); Laszlo Karai, Kensington, MD (US)

(73) Assignee: The United States of America as represented by the Secretary of the Department of Human Services, Washington, DC (US)

( * ) Notice: Subject to any disclaimer, the term of this patent is extended or adjusted under 35 U.S.C. 154(b) by 27 days.

(21) Appl. No.: 12/776,304

(22) Filed: May 7, 2010

(65) Prior Publication Data

US 2010/0222385 A1    Sep. 2, 2010

Related U.S. Application Data

(63) Continuation of application No. 10/472,874, filed as application No. PCT/US01/09425 on Mar. 22, 2001, now abandoned.

(51) Int. Cl.
*A01N 43/40* (2006.01)
*A01N 43/02* (2006.01)
*A61K 31/445* (2006.01)
*A61K 31/335* (2006.01)

(52) U.S. Cl. ........................... 514/315; 514/350
(58) Field of Classification Search .................. 514/315, 514/450
See application file for complete search history.

(56) References Cited

U.S. PATENT DOCUMENTS

| 4,920,209 | A | 4/1990 | Davis et al. |
| 5,232,684 | A | 8/1993 | Blumberg et al. |
| 5,962,532 | A | 10/1999 | Campbell et al. |
| 6,194,191 | B1 | 2/2001 | Zhang et al. |

FOREIGN PATENT DOCUMENTS

| WO | WO 90/14083 A1 | 11/1990 |
| WO | WO 98/20867 A1 | 5/1998 |
| WO | WO 00/50387 A1 | 8/2000 |

OTHER PUBLICATIONS

Of Panchal et al. (Tech in Reg Anesthesia and Pain Mgmt vol. 4, 3, 2000, 137-142).*
Paice et al. (Cancer Pain and Management, 1987, 6, 131-158).*
Bevan, S., et al., "Sensory neuron-specific actions of capsaicin: mechanisms and applications," *TiPS*, Aug. 1990, vol. 11, pp. 330-333.
Broberger, C., et al., "Increased spinal cholecystokinin activity after systemic resiniferatoxin: electrophysiological and in situ hybridization studies," *Pain*, 2000, vol. 84, pp. 21-28.
Caterina, M., et al., "The capsaicin receptor: a heat-activated ion channel in the pain pathway," *Nature*, Oct. 23, 1997, vol. 389, pp. 816-824.
Coghill, R., et al., "Pain Intensity Processing Within the Human Brain: A Bilateral, Distributed Mechanism," *J. Neurophysiol.*, 1999, vol. 82, pp. 1934-1943.
Cruz, F.; "Desensitization of bladder sensory fibers by intravesical capsaicin or capsaicin analogs. A new strategy for treatment of urge incontinence in patients with spinal detrusor hyperreflexia or bladder hypersensitivity disorders"; 1998, *Int. Urogynecol J. Pelvic Floor Dysfunct.*, vol. 9, No. 4, pp. 214-220.
Dickenson, A., et al.; "Antinociception produced by capsaicin: spinal or peripheral mechanism?" 1990, *European Journal of Pharmacology*, vol. 187, pp. 225-233.
Farkas-Szallasi, T., et al., "Vanilloid receptor is independent of the messenger plasticity that follows systemic resiniferatoxin administration," *Brain Res.*, May 6, 1996, vol. 719, Nos. 1-2, pp. 213-218.
Iadarola, M., et al., "Good Pain, Bad Pain," *Science*, Oct. 10, 1997, vol. 278, pp. 239-240.
Jagger, A., et al., "Reduced vagal sensory innervation of the small intestinal myenteric plexus following capsaicin treatment of adult rats," *Neuroscience Letters*, 1997, vol. 236, pp. 103-106.
Jancsó, G., et al., "Pharmacologically induced selective degeneration of chemosensitive primary sensory neurons," *Nature*, Dec. 1977, vol. 270, pp. 741-743.
Karai, L., et al., "Evaluation of Intraganglionic Resiniferatoxin (RTX) Injection for Pain Control," *Society for Neuroscience Abstracts*, Nov. 10-15, 2001, vol. 27, No. 1, Abtract only, 1 pg.
Karai, Laszlo, et al., "Deletion of vanilloid receptor 1-expressing primary afferent neurons for pain control," *The Journal of Clinical Investigation* (May 2004) 113(9): 1344-1352.
Mannes, A. et al.; "Resinferatoxin, a potent TRPV1 agonist: Intrathecal administration to treat severpain associated with advanced cancer-case report"; 2010, *Annual Meeting of the American Pain Society*, 1 page abstract.
Mantyh, Patrick W. et al.; "Inhibition of Hyperalgesia by Ablation of Lamina I Spinal Neurons Expressing the Substance P Receptor"; 1997, *Science*, vol. 278, pp. 275-280.
Mitchell, K. et al.; "Prolonged analgesic effect of RTX on A-delta type II fibers following peripheral administration"; 2010, *Annual Meeting of the American Pain Society*, 1 page abstract.
Nagy, J., et al., "A re-evaluation of the neurochemical and antinociceptive effects of intrathecal capsaicin in the rat," *Brain Research*, 1981, vol. 211, pp. 497-502.

(Continued)

*Primary Examiner* — Sreeni Padmanabhan
*Assistant Examiner* — Uma Ramachandran
(74) *Attorney, Agent, or Firm* — Kilpatrick Townsend & Stockton LLP

(57) ABSTRACT

The present invention provides methods and kits for the selective ablation of pain-sensing neurons. The methods comprise administration of a vanilloid receptor agonist to a ganglion in an amount that causes death of vanilloid receptor-bearing neurons. Accordingly, the present invention provides methods of controlling pain and inflammatory disorders that involve activation of vanilloid receptor-bearing neurons.

14 Claims, 2 Drawing Sheets

OTHER PUBLICATIONS

Olah, Z., et al., "Ligand-Induced Dynamic Membrane Changes and Cell Deletion Conferred by Vanilloid Receptor 1," *The Journal of Biological Chemistry*, vol. 276, No. 14, Apr. 6, 2001, pp. 11021-11030.

Ossipov, M., et al., "Lack of involvement of capsaicin-sensitive primary afferents in nerve-ligation injury induced tactile allodynia in rats," *Pain*, 1999, vol. 79, pp. 127-133.

Pabst, M.A. et al.; "Ablation of capsaicin sensitive afferent nerves impairs defence but not rapid repair of rat gastric"; 1993, *Gut*, vol. 34, pp. 897-903.

Palermo, N., et al., "Selective neurotoxic action of capsaicin on glomerular C-type terminals in rat substantia gelatinosa," *Brain Research*, 1981, vol. 208, pp. 506-510.

Russell, L., et al., "Effect of Intrathecal and Subepineural Capsaicin on Thermal Sensitivity and Autotomy in Rats," *Pain*, 1986, vol. 25, pp. 109-123.

Szabo, T., et al., "Epidural resiniferatoxin induced prolonged regional analgesia to pain," *Brain Research*, 1999, vol. 840, pp. 92-98.

Szallasi, A., et al., "Effects of systemic resiniferatoxin treatment on substance P mRNA in rat dorsal root ganglia and substance P receptor mRNA in the spinal dorsal horn," *Brain Research*, 1999, vol. 815, pp. 177-184.

Szallasi, A., et al., "Vanilloid receptors: new insights enhance potential as a therapeutic target," *Pain*, 1996, vol. 68, pp. 195-208.

Szallasi, A., et al., "Resiniferatoxin-type phorboid vanilloids display capsaicin-like selectivity at native vanilloid receptors on rat DRG neurons and at the cloned vanilloid receptor VR1," *British Journal of Pharmacology*, 1999, vol. 128, pp. 428-434.

Szallasi, A., et al., "The Cloned Rat Vanilloid Receptor VR1 Mediates Both R-Type Binding and C-Type Calcium Response in Dorsal Root Ganglion Neurons," *Molecular Pharmacology*, 1999, vol. 56, pp. 581-587.

Szallasi, A., et al., "New perspectives on enigmatic vanilloid receptors"; 2000, *Trends Neurosci.*, vol. 23, pp. 491-497.

Szallasi, A., et al., "Vanilloid Receptor Ligands"; 2001, *Drugs & Aging*, vol. 18, No. 8, pp. 561-573.

Szolcsanyi, J. et al.; "Effect of CP-96, 345 a Non-Peptide Substance P Anta"; 1993, *Regulatory Peptides*, vol. 2, No. 46, pp. 437-439.

Tominaga, M., et al., "The Cloned Capsaicin Receptor Integrates Multiple Pain-Producing Stimuli," *Neuron*, Sep. 1998, vol. 21, pp. 531-543.

Yaksh, T., et al., "Intrathecal Capsaicin Depletes Substance P in the Rat Spinal Cord and Produces Prolonged Thermal Analgesia," *Science*, Oct. 26, 1979, vol. 206, pp. 481-483.

Yamakuni, Hisashi et al.; "Resiniferatoxin antagonizes cisplatin-induced emesis in dogs and ferrets"; 2002 *European Journal of Pharmacology*, vol. 442, No. 3, pp. 273-278.

\* cited by examiner

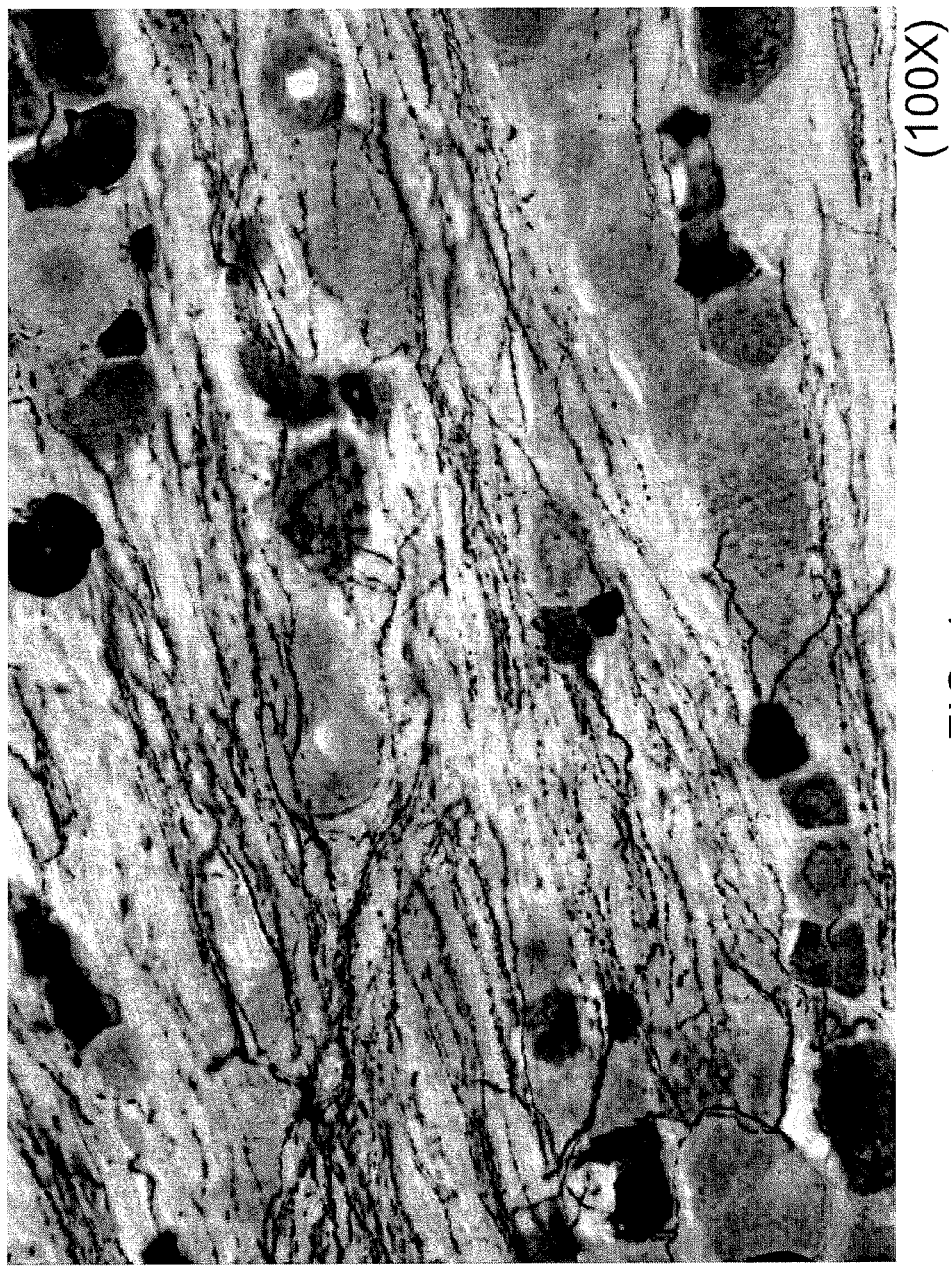
FIG. 1 (100X)

FIG. 2 (100X)

SELECTIVE ABLATION OF PAIN-SENSING NEURONS BY ADMINISTRATION OF A VANILLOID RECEPTOR AGONIST

CROSS-REFERENCES TO RELATED APPLICATIONS

This application is a continuation of co-pending U.S. patent application Ser. No. 10/472,784 filed Mar. 18, 2004, which is a 371 national stage application of PCT application no. PCT/US01/09425 filed Mar. 22, 2001, both of which are incorporated herein by reference.

BACKGROUND OF THE INVENTION

Current analgesic therapies often fall short of therapeutic goals and typically have unacceptable side effects. In many chronic pain syndromes, such as those subsequent to neuropathic injury, pain is not well controlled by any currently available method. The sensation of pain is transduced in the periphery by pain-sensing, i.e. nociceptive, C- and A-delta primary afferent neurons. These neurons have a peripheral nerve ending in the skin or deep tissues and a central terminal that makes synaptic contact with second order neurons in the spinal cord dorsal horn. The impulse is processed locally for activation of withdrawal reflexes and relayed to the brain for conscious perception and contextually relevant integrated responses.

Vanilloid receptor-1 (VR1) is a multimeric cation channel prominently expressed in nociceptive primary afferent neurons (see, e.g., Caterina et al., *Nature* 389:8160824, 1997; Tominaga et al., *Neuron* 531-543, 1998). Activation of the receptor typically occurs at the nerve endings via application of painful heat (VR1 transduces heat pain) or during inflammation or exposure to vanilloids. Activation of VR1 by an agonist, such as resiniferatoxin or capsaicin, results in the opening of calcium channels and the transduction of pain sensation (see, e.g., Szalllasi et al., *Mol. Pharmacol.* 56:581-587, 1999.) After an initial activation of VR1, VR1 agonists desensitize VR1 to subsequent stimuli. This desensitization phenomenon has been exploited in order to produce analgesia to subsequent nociceptive challenge. For example, it has been shown that topical administration of resiniferatoxin (RTX), which is a potent vanilloid receptor agonist, at the nerve endings in the skin triggers a long-lasting insensitivity to chemical pain stimulation. Furthermore, it has been shown that both subcutaneous and epidural administration of the RTX produce thermal analgesia when administered to rats, with no restoration of pain sensitivity for over 7 days (see, e.g., Szabo et al., *Brain Res.* 840:92-98, 1999).

In these studies, however, the VR1 agonist was not administered directly to the nerve ganglion and the analgesic effect was reversible. Spatially, the peripheral $Ca^{2+}$ toxicity is far removed from the neuronal perikarya in the ganglion so that application to the skin does not cause cell death. The present invention is based on the discovery that administration of VR-1 receptor agonist to the ganglion at the level of the neuronal cell body causes neuronal cell death and moreover, that the resulting selective ablation of VR1-containing neurons provides a treatment for chronic pain.

The effects of intrathecal capsaicin on thermal sensitivity in rats has also been investigated. The results, however, have been conflicting (Nagy et al., *Brain Res.* 211:497-502, 1981; Palermo et al., *Brain Res.* 208:506-510; Yaksh et al., *Science* 206:481-483, 1979; and Russell et al., *Pain* 25:109-123, 1986). Russell et al. observed no thermal analgesia, although in three previous studies, at least some degree of thermal analgesia was observed. The conflicting results raised a number of issues such as the possibility of complications in data interpretation resulting from spinal cord damage from cannula implantation, or solvent toxicity problems. Russell et al. therefore used a non-toxic solvent for capsaicin administration to rats and additionally, performed partial laminectomies to allow direct visualization of the cauda equina and thus insure drug delivery to the spinal fluid. No thermal analgesia was demonstrated and the authors concluded that intrathecal capsaicin administration is not a reliable method for producing thermal analgesia in the rat. The present inventors now resolve this controversy with the surprising discovery that intrathecal injection of a vanilloid receptor agonist such that the agonist contacts the neuronal cell body in an amount sufficient to cause $Ca^{2+}$ influx, results in selective ablation of the neuron, and therefore is an effective therapy for chronic pain.

Recent studies have also shown that pain sensing C-fibers appear to participate in or exacerbate a variety of chronic diseases such as chronic pancreatitis, herpes infections, inflammatory or irritable bowel disease and rheumatoid arthritis. Generally, these chronic diseases have an inflammatory component in which the C-fibers play a role. The present invention therefore also provides a method of destroying C-fiber neurons that contribute to chronic disease syndromes, thus providing a method to ameliorate or resolve chronic inflammatory conditions. In addition, the ability to selectively kill VR-1-expressing neurons using the methods of the invention also provides a therapy for selectively removing neurons that are reservoirs of virus in chronic viral infections such as Herpes virus infection.

SUMMARY OF THE INVENTION

The present invention is based on the surprising discovery that direct application of a vanilloid receptor agonist into the neuron cell body contained in a ganglion opens calcium channels in VR1-expressing neuronal perikarya, triggering a cascade of events leading to cell death. Accordingly, the present invention provides methods of controlling pain and inflammatory disorders that involve activation of vanilloid receptor-bearing neurons. In particular, selective deletion of nociceptive primary afferent neurons by intraganglionic or intrathecal administration of the vanilloid agonist, e.g., resiniferatoxin (RTX) interrupts the signaling pathway and blocks pain sensation and neurogenic inflammation. This selective application can be used for treatment-resistant trigeminal neuralgia, atypical facial pain, certain types of neuropathic pain, for pain management in end-stage disease or palliative care, and for treatment of chronic pain that occurs in chronic infections.

Thus, the invention provides a method of selectively ablating pain-sensing neurons from a ganglion, said method comprising intraganglionic administration of a vanilloid receptor agonist to a ganglion selected from the group consisting of a dorsal root ganglion, a trigeminal ganglion, or an autonomic ganglion in an amount sufficient to ablate the neurons.

In some embodiment, the vanilloid receptor 1 agonist is administered to a patient suffering from chronic pain. Often, the vanilloid receptor agonist is selected from the group consisting of a resiniferatoxin or a capsaicin, such as ovanil. Preferably, the VR1 agonist is a resiniferatoxin.

In one embodiment, intraganglionic administration comprises direct injection into the ganglion.

In an alternative embodiment, intraganglionic administration comprises injection into the nerve root.

In one embodiment, the amount that is sufficient to ablate the neurons is from 50 nanograms to 50 micrograms. Often the amount is from about 500 nanograms to about 50 micrograms.

In some embodiments, the method further comprises administration of a local anesthetic, often lidocaine or bupivacaine.

In another aspect, the invention provides a method of selectively ablating pain-sensing neurons from a ganglion, said method comprising intrathecal administration of a vanilloid receptor agonist to a dorsal root ganglion in an amount sufficient to ablate the neurons. In some embodiments, intrathecal administration of the VR1 agonist is with the proviso that the VR1 agonist is not administered to a rat or other rodent.

In a preferred embodiment, the VR1 agonist is a resiniferatoxin.

In one embodiment, the amount that is sufficient to ablate the neurons is from 100 nanograms to 500 micrograms. Often, the amount is from about 500 nanograms to about 500 micrograms.

In some embodiments, the method further comprises administration of a local anesthetic, often lidocaine or bupivacaine.

In another aspect, the invention provides a kit for selectively ablating pain sensing neurons from a dorsal root, autonomic, or trigeminal ganglia, said kit comprising a compartment containing a vanilloid receptor agonist in an amount sufficient to ablate the neurons and instructional materials describing how to use the kit. Such a kit can also contain a local anesthetic. In particular embodiments, the vanilloid receptor agonist is a resiniferatoxin.

BRIEF DESCRIPTION OF THE DRAWINGS

FIG. 1 is a micrograph of CGRP immunochemistry in an untreated trigeminal ganglion.

FIG. 2 is a micrograph of CGRP immunochemistry in a treated trigeminal ganglion.

DETAILED DESCRIPTION

1. Introduction

This invention pertains to the surprising discovery that administration of vanilloid receptor agonist to a peripheral neuron ganglion is toxic to VR-1 expressing neurons and is therefore useful to selectively treat acute and chronic pain, while at the same time not significantly affecting other somatosensory functions such as position sense, light touch, hair movement, pressure or mechanical vibration as well as mechanical pinch sensitivity. The neurons that subserve these sensations do not make VR-1 and thus they are not sensitive to ablation by vanilloid agonist treatment. The selective ablation of pain-sensing neurons in these ganglia is useful for the treatment of chronic pain, particularly including, but not limited, to neuropathic pain resulting from injury to specific nerves; pain associated with cancer, such as pain resulting from bone metastases to the spinal column in prostate cancer; pain associated with inflammatory diseases such as acute pancreatitis and pain associated with chronic ganglionic viral infections particularly with infection by members of the Herpes virus family such as Herpes zoster or Herpes simplex I and II.

Delivery of VR1 agonists to ganglionic neuronal cell bodies is not only an effective therapy for chronic pain, but can also be used to treat other chronic inflammatory conditions where persistent inflammation causes severe exacerbation of the underlying disease or may be the cause of the inflammatory condition. For example, intraganglionic VR1 agonist can be used to treat herpes virus infections or pain disorders caused by herpes virus infection such as post-herpetic neuralgia (shingles). Herpes viruses enter a latent state in the dorsal root ganglia, and the C-fiber neurons are an important reservoir of the latent virus. Upon stress or reactivation the virus exits the latent state and begins replication. Viral particles are transported down the axon where they erupt on the skin. In many cases the eruption can be very painful, and further, can present additional problems for immunocompromised patients or elderly patients. Although there has been some progress in antiviral therapy, it remains difficult to effectively treat this condition. Because the C-fiber neuronal cell bodies express VR1 receptor, the present invention therefore also provides a method of selectively removing the neurons that act as a viral reservoir. Upon administration of a VR1 agonist to the neuronal cell body, death occurs rapidly, and the virus cannot enter a replicative state. Thus, the invention also provides a treatment for chronic viral infection, e.g., Herpes virus infection, with limited impact on a patient's ability to sense pain (except in the dermatomes innervated by the treated ganglia), and provides very effective pain relief without compromising other sensory functions.

2. Definitions

The term "VR1 agonist" as used herein refers to a to a compound that binds to VR1 and stimulates calcium uptake. Typically, VR1 agonists comprise a vanilloid ring that is important for agonist activity.

The term "administering" incorporates the common usage and refers to any appropriate means to give a pharmaceutical to a patient, taking into consideration the pharmaceutical composition and the preferred site of administration (e.g., in one embodiment, the pharmaceutical composition of the invention is injected into the subarachnoid space as an aqueous solution).

A "patient" as used herein is synonymous with "subject" and refers to any mammal including, but not limited to, horse, cow, sheep, goat, pig, dog, cat, rat, mouse, guinea pig, and primate. In a preferred embodiment, the mammal is a human.

The term "basal nociceptive responses" incorporates its common usage and refers to baseline responses to nociceptive, or painful, stimuli.

The terms "chronic pain" and "acute pain" incorporate their common usages; subjective (e.g., clinical diagnosis) and other objective means (e.g., laboratory tests, PET) to determine the presence of chronic pain and/or acute pain, and to distinguish between these two distinct categories of pain, are described in detail, below.

The term "vanilloid receptor 1" or "VR1" refers to a ligand-gated cation channel, distantly related to the TRP (transient release potential) proteins, that can be activated by vanilloids, heat, and protons. A VR1 agonist binds to VR1 and activates the VR1 cation channel.

The term "hyperalgesia" refers to an increased response to a stimulus that is normally painful (see, e.g., Bonica (1990) infra). Its presence is recognized as a symptom of chronic pain (i.e., its presence is associated with or is a sequelae of chronic pain).

The term "pharmaceutically acceptable excipient" incorporates the common usage and refers to includes any suitable pharmaceutical excipient, including, e.g., water, saline, phosphate buffered saline, Hank's solution, Ringer's solution, dextrose/saline, glucose, lactose, or sucrose solutions, magnesium stearate, sodium stearate, glycerol monostearate, glycerol, propylene glycol, ethanol, and the like.

The term "subarachnoid space" or cerebral spinal fluid (CSF) space incorporates the common usage refers to the anatomic space between the pia mater and the arachnoid membrane containing CSF.

The term "intrathecal administration" refers to administration of a compositions directly into the spinal subarachnoid space.

"Intraganglionic administration" as used herein refers to administration to a ganglion. Intraganglionic administration can be achieved by direct injection into the ganglion and also includes selective nerve root injections, in which the compound passes up the connective tissue sleeve around the nerve and enters the ganglion from the nerve root just outside the vertebral column. Often, intraganglionic administration is used in conjunction with an imaging technique, e.g., employing MRI or x-ray contrast dyes or agents, to visualize the targeted ganglion and area of administration.

The term "treating" refers to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; slowing in the rate of degeneration or decline; making the final point of degeneration less debilitating; improving a patient's physical or mental well-being; or, in some situations, preventing the onset of the symptom or condition, e.g., pain. The treatment or amelioration of symptoms can be based on any objective or subjective parameter; including, e.g., the results of a physical examination and/or a psychiatric evaluation, or, simply an improvement in the patient's sense of well-being. For example, the methods of the invention selectively treats chronic pain by ameliorating the hyperalgesia associated with chronic pain, while not significantly affecting non-pain sensory functions such as proprioception, muscle and tendon stretch, light touch, vibration sense, motion sensitive mechanoreceptors that innervate hair follicles and pressure sense.

3. Distinguishing Chronic from Acute Pain

Pain is always subjective and can have physiologic, pathophysiologic, psychologic, emotional, and affective dimensions. Pain causation can be broadly categorized as organic or psychogenic. Basically, two types of pain exist—acute pain and chronic pain. Each possibly is mediated by anatomically different nerves. Each type of pain has a different physiologic role. For example, the ability to perceive and respond to "acutely" painful stimuli, which usually has the potential to cause tissue damage, serves a protective role for the individual. Many treatments for acute pain cannot ameliorate chronic pain (this, in fact, is used as one means to objectively identify "chronic" versus "acute" pain, as discussed below). There presently exists no clinically accepted effective therapy to treat chronic pain without the unwanted side effect of significantly dampening protective acute pain responses. The present invention provides for targeted removal of neurons, thus limiting the loss of the acute pain response to those acute pain sensations transduced by the particular neurons.

Accordingly, in some embodiments, the methods of the invention comprise selective ablation of neurons in patients or subjects suffering from chronic pain. In some embodiments, such as treatment of chronic pain in a young nerve injury patient, one or two ganglia, or a particular nerve root are targeted for treatment using the methods of the invention, thus providing limited damage to acute pain responses.

Diagnosing and Assessing Chronic Pain

The invention provides methods of treating chronic pain while at the same time not significantly affecting the ability to respond to acutely painful, and potentially harmful, stimuli. Thus, proper diagnosis of chronic pain is necessary both to practice and to assess the success of the compositions and methods of the invention. Means to diagnosis chronic pain include classical clinical and psychological evaluations, which can be augmented by various laboratory procedures, as described herein. Such means are well-described in the medical/scientific and patent literature; some illustrative examples are provided below.

One criteria to diagnose a "chronic" pain is whether the pain persists for a month beyond the usual course of an acute disease or a reasonable time for an injury to heal. This evaluation is made by the clinician on a case by case basis. Acute diseases or injuries can heal in 2, 3, or, at most, 6 weeks, depending on the nature of the condition or injury, the age and health of the patient, and the like. For example, a simple wrist fracture can remain painful for a week to ten days; however, if pain persists longer than this period, a dystropathy could be developing which will be irreversible if not treated. See, e.g., Bonica, et al., (1990) "Management of Pain," 2nd Ed., Vol. I, Lea & Feibiger, Phil., Pa.; Wall and Melzack (1994) "Textbook of Pain," Churchill Livingstone, NY. Accordingly, a chronic pain is diagnosed by the practitioner based on clinical and laboratory results, depending on the particular condition or injury, patient, and the like (see also, e.g., Russo (1998) *Annu. Rev. Med.* 49:123-133).

Another means to identify a "chronic" pain is by diagnosis of a pathologic process (which is usually also chronic) known to produce or be associated with chronic pain. Such conditions are well characterized and include, e.g., chronic pain syndrome (see, e.g., Clifford (1993) *Can. Fam. Physician* 39:549-559), arthralgia, arthritis (e.g., osteoarthritis and rheumatoid arthritis), causalgia, hyperpathia, neuralgia, neuritis, radiculagia, fibromyalgia (see, e.g., Simms (1998) *Am. J. Med. Sci.* 315:346-350), orofacial pain and temporomandibular disorders (see, e.g., Binderman (1997) *Curr. Opin. Periodontol.* 4:144-15), reflex sympathetic dystrophy (see, e.g., Dangel (1998) *Paediatr. Anaesth.* 8:105-112, chronic back pain, certain cancers, and the like.

Chronic pain is also associated with particular injuries to the nerves. These include, e.g., nerve transection (traumatic or surgical), chronic abnormal pressure on a nerve, chemical (e.g., formalin) destruction of nerve tissue, and the like.

Chronic pain can also be distinguished from acute pain by its non-responsiveness to pharmacologic therapies known to significantly ameliorate or abate acute pain. When pain is initially diagnosed as acute or of unknown etiology, the clinician typically administers one of several analgesics known in the art to be effective for acute pain, such as, e.g., a non-steroid anti-inflammatory drug (NSAID), such as, e.g., aspirin, ibuprofen, propoxyphene, tramadol, acetaminophen and the like (see, e.g., Tramer (1998) Acta Anaesthesiol. Scand. 42:71-79). If there is no significant amelioration of pain, as assessed by the clinician, over an approximately six week period, then a provisional diagnosis of chronic pain can be made. Ultimately, as discussed above, a diagnosis of chronic pain depends upon determination as to whether pain would be expected, given each individual situation.

Other treatments to which chronic pain is also typically incompletely or totally unresponsive include tricyclic antidepressant administration, psychotherapy, or alternative medicines, such as acupuncture, biofeedback, and the like.

Laboratory, radiographic and other types of imaging procedures may also be used to diagnose chronic pain. In particular, positron emission tomography, or PET, now allows the clinician to objectify such otherwise merely subjective symptoms, including chronic pain (see, e.g., Reiss (1998) Fortschr. Med. 116:40-43; Di Piero (1991) Pain 46:9-12).

4. Vanilloid Receptor Agonists

VR1 agonists as defined herein bind to the VR1 receptor and stimulate calcium activity. VR1 agonists are typically characterized by the presence of a vanilloid moiety that mediates binding and activation of the receptor. Any number of VR1 receptor agonists are useful for practicing the methods of the invention. Compounds that act as VR1 receptor agonists include resiniferatoxin and other resiniferatoxin-like complex polycyclic compounds such as tinyatoxin, capsaicin and other capsaicin analogs such as ovanil, and other compounds that include a vanilloid moiety that mediates binding and activation of VR1. In some instances, such as low pH, compounds that lack a vanilloid moiety, e.g., anandamide and the eicosanoids prostacyclin and $PGE_2$ can also functionally activate VR1.

Resiniferatoxin

In one embodiment, RTX is used as the vanilloid receptor agonist. RTX, is unlike the structurally related phorbol esters, acts as an ultrapotent analog of capsaicin, the pungent principle of the red pepper. RTX is a tricyclic diterpene isolated from *Eurphorbia resinifera*. RTX induces pain, hypothermia, and neurogenic inflammation; the acute responses are followed by desensitization to RTX and by cross-desensitization to capsaicin. A homovanillyl group is an important structural feature of capsaicin and the most prominent feature distinguishing resiniferatoxin from typical phorbol-related compounds. Naturally occurring or native RTX has the following structure:

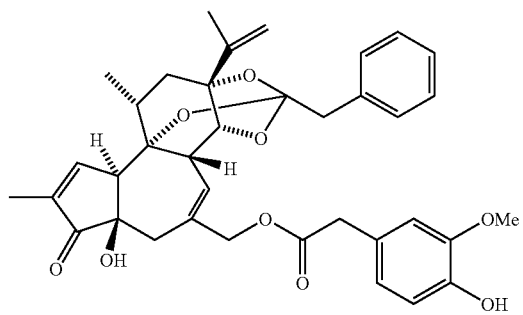

RTX and analog compounds such as tinyatoxin as well other compounds, e.g., 20-homovanillyl esters of diterpenes such as 12-deoxyphorbol 13-phenylacetate 20-homovanillate and mezerein 20-homovanillate, are described, for example, in U.S. Pat. Nos. 4,939,194; 5,021,450; and 5,232,684. Other resiniferatoxin-type phorboid vanilloids have also been identified (see, e.g., Szallasi et al., *Brit. J. Phrmacol.* 128:428-434, 1999). Often, the $C_{20}$-homovanillic moiety, the $C_3$-keto group and the ortho-ester phenyl group on ring C are important structural elements for activity of RTX and its analogs. As used herein, "a resiniferatoxin" or "an RTX" refers to naturally occurring RTX and analogs of RTX, including other phorbol vanilloids with VR1 agonist activity.

Capsaicin

Capsaicin is a natural product in capsicum peppers that mediates the "hot" sensation characteristic of these peppers. As used herein, "a capsaicin" or "capsaicinoids" refers to capsaicin and capsaicin-related or analog compounds. Naturally occurring or native capsaicin has the structure:

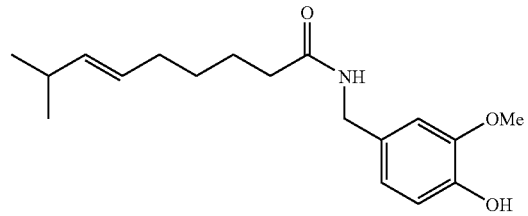

A number of analogs of capsaicins are known in the art including vanillylacylamides, homovanillyl acylamides, carbamate derivatives, sulfonamide derivatives, urea derivatives, aralkylamides and thioamides, aralkyl aralkanamides, phenylacetamides and phenylacetic acid esters are known in the art. In one embodiment, the capsaicin analog olvanil (N-vanillyl-9-octadecenamide) is used in the methods of the invention. Examples of capsaicin and capsaicin analogs are described, for example, in the following patents and patent applications: U.S. Pat. No. 5,962,532; U.S. Pat. No. 5,762,963; U.S. Pat. No. 5,221,692; U.S. Pat. No. 4,313,958; U.S. Pat. No. 4,532,139; U.S. Pat. No. 4,544,668; U.S. Pat. No. 4,564,633; U.S. Pat. No. 4,544,669; and U.S. Pat. Nos. 4,493,848; 4,532,139; 4,564,633; and 4,544,668.

Other VR1 Agonists

Other VR1 agonists (see, e.g., WO 00/50387) can also be used to selectively ablate C-fiber neurons. Such compounds comprise a vanilloid moiety that mediates binding and activation of VR1. These compounds include compounds having modifications on the $C_{20}$-homovanillic moiety, the $C_3$-carbonyl, and the ortho-ester phenyl moiety.

Useful VR1 agonists for practicing the invention can be readily identified using standard methodology. The methodology includes such assessments as measurement of binding to a compound to VR1 and measurement of the ability of the compound to stimulate $Ca^{2+}$ influx. The compound can also be assessed for the ability to kill cells that express the vanilloid receptor. These measurements can be performed using methods known to those of skill in the art.

The ability of a VR1 agonist to bind VR1-bearing cells or membranes can be measured directly or, more typically, in a competition analysis with a known binding compound such as RTX. VR1 binding assays are described in a number of publication, for example, in various U.S. patents and other publications (e.g., WO 00/50387, U.S. Pat. No. 5,232,684, supra; Szallasi et al., *Molec. Pharmacol.* 56:581-587, 1999). In an exemplary assay, binding activity of a compound containing a vanilloid moiety can be assessed be measuring the ability of the compound to displace bound [$^3$H]RTX from the VR1 receptor. The analysis can be performed using any cell or cell membrane that has VR1 receptors. Often, VR1-expressing transfectants or membrane from the spinal cord are used. The results are usually expressed in terms of Ki values that represent the concentration of the non-radioactive ligand that displaces half of the bound labeled RTX. Preferred VR1 agonists, e.g., RTX, typically have a 10-fold, often a 100-fold, preferably a 1000-fold higher binding affinity for VR1 than native, i.e., the naturally occurring, capsaicin.

In order to identify VR1 agonists, binding assays are typically performed in conjunction with functional assessments that measure the ability of a compound to stimulate changes in membrane potential or changes in calcium influx. Changes in membrane potential or calcium influx can be determined using a variety of assays well known to those in the art. For example, VR1-expressing cells such as neurons from the dorsal root ganglion or VR1 transfectants can be analyzed by patch clamping for changes in whole cell currents that occur upon exposure of the compound being tested for VR1 activity (see, e.g., the Example section below and Caterina et al., Nature 389:816-824, 1997). Another commonly used method to assess VR1 agonist activity is to measure the uptake of calcium using various assays to measure intracellular calcium concentration. For example, calcium flux can be measured by assessment of the uptake of $^{45}Ca^{2+}$ or by using fluorescent dyes such as fura-2. For example, a dye such as fura-2, which undergoes a change in fluorescence upon binding a single $Ca^{2+}$ ion, is loaded into the cytosol of VR1-expressing cells. Upon exposure to VR1 agonist, the increase in cytosolic calcium is reflected by a change in fluorescence of fura-2 that occurs when calcium is bound. Such measurements can also be used to assess the ability of a VR1 agonist to mobilize intracellular calcium stores from the endoplasmic reticulum (ER). In preferred embodiments, VR1 agonists stimulate both a release of $Ca^{2+}$ from the ER and an influx of calcium across the cell membrane.

VR1 agonists of this invention are analyzed for the ability to elicit cell death. In these assays, VR1-expressing cells are exposed to VR1 agonist. VR1-mediated cell death is determined by using morphological assessments and/or staining with vital dyes such as trypan blue (see, e.g., the Examples section and Caterina et al., supra). Preferred VR1 agonists for use in the invention typically are 100 times, often 1000 times more potent than native capsaicin.

Additional compounds e.g., anandamide, and certain eicosanoids such as prostacyclin and PGE2, can activate VR1, but lack a vanilloid moiety. Such compounds can and that are of use in the methods of the invention can also be identified by determining the ability of a compound, to stimulate calcium uptake and/or cause cell death. Such compounds are typically identified in an assay that compares activation of VR1 in response to the compound to activation of VRA in response to a known VR1 agonist, e.g., capsaicin or RTX. comparison to a VR1 agonist that comprises a vanilloid moiety, often in a competitive functional assay. Preferred compounds are 100-fold, preferably 1000-fold, more potent in activating VR1-induced calcium mobilization in comparison to native capsaicin.

5. Administration of VR1 Agonists

VR1 agonists, such as RTX or olvanil, are formulated as pharmaceuticals to be used in the methods of the invention to treat chronic pain by selective ablation of VR1-expressing neurons. Any VR1 agonist that causes an increase in intracellular calcium, preferably by causing both a transmembrane calcium flux and release of calcium from the ER, and kills VR1-expressing cells can be used as a pharmaceutical in the invention. Routine means to determine VR1 agonist drug regimens and formulations to practice the methods of the invention are well described in the patent and scientific literature, and some illustrative examples are set forth below.

Routes of Administration

The VR1 agonists can be administered by any means that delivers the VR1 agonist into the vicinity of the nociceptive primary afferent neuronal cell body. These routes of administration include intrathecal administration and intraganglionic administration directly into the ganglion or performed by selective nerve root injections. in which the compound passes up the connective tissue sleeve around the nerve and enters the ganglion from the nerve root just outside the vertebral column (see, e.g., TEXTBOOK OF PAIN, Wall and Melzack, Eds. Harcourt Brace, 4th Ed, 1999).

In one embodiment, the VR1 agonist is injected directly into a ganglion or at the nerve root using methods standard neurosurgical techniques. Often, administration is performed using image analysis using MRI or x-ray contrast dyes, to provide for direct delivery to the perikarya. For example, the procedure can be performed in conjunction with procedures known in the art, such as CAT scan, fluoroscopy, or open MRI.

In another embodiment, the agonist is administered intrathecally, typically in a isobaric or hyperbaric pharmaceutically acceptable excipient as further described below. Means to administer solutions into the subarachnoid space, i.e., intrathecally, into the CSF, are well known in the art; see, e.g., Oyama, T., U.S. Pat. No. 4,313,937.

Determining Dosing Regimens

The pharmaceutical formulations of the invention can be administered in a variety of unit dosage forms, depending upon the particular condition or disease, the degree of chronic pain, the general medical condition of each patient, the method of administration, and the like. In one embodiment, the VR1 agonist is administered in a pharmaceutically acceptable excipient at a dose of complete with amount. Details on dosages are well described in the scientific and patent literature, see, e.g., the latest edition of Remington's Pharmaceutical Sciences, Maack Publishing Co, Easton Pa.

The exact concentration of VR1 agonist in a given dose, or the "therapeutically effective dose" is determined by the medical practitioner, as discussed above. The dosage schedule, i.e., the "dosing regimen," will depend upon a variety of factors, including the amount of chronic pain present, the duration of the pain, the stage and severity of the disease or condition associated with the chronic pain (if any), and the general state of the patient's health, physical status, age and the like. The state of the art allows the clinician to determine the dosage regimen for each individual patient and, if appropriate, concurrent disease or condition treated. The illustrative example provided below can be used as guidance to determine the dosage regimen, i.e., dose schedule and dosage levels administered when practicing the methods of the invention.

Typically, VR1 agonists to a particular ganglion are administered to create a temporary environment from about 1 to 5 minutes achieved by injection of the agonist. Based on objective and subjective criteria, as discussed herein, any dosage can be used as required and tolerated by the patient. Multiple administrations can also be performed as required. For intraganglionic administration to a dorsal root or autonomic ganglion, a typical volume injected is from 50 to 300 microliters delivering a total amount of VR1 agonist that ranges from about 50 nanograms to about 50 micrograms. Often the amount administered is from 200 ng to 1 ug. The VR1 can be administered as a bolus or infused over a period of time, typically from 1 to 5 minutes. For intraganglionic administration to a trigeminal ganglion, a volume of from about 100 microliters to about 500 microliters is typically used to delivered from about 50 nanograms to about 50 micrograms of VR1 agonist. The VR1 agonist can be infused over a length of time from about 1 to 5 minutes, or can be delivered as one or more boluses. Dosages in the ranges of 100 nanograms to 500 micrograms are often used. For intrathecal administration, an amount from about 0.5 to 5 ccs, often 3 ccs are injected into the subarachnoid space. The total amount of VR1 agonist in the injected volume is usually from about 500 nanograms to about 500 micrograms.

VR1 agonist can be prepared as pharmaceutical compositions by combination with appropriate medical carriers or diluents. Examples of aqueous solutions that can be used in VR1 formulations include, e.g., water, saline, phosphate buffered saline, Hank's solution, Ringer's solution, dextrose/saline, glucose solutions and the like. The formulations can contain pharmaceutically acceptable auxiliary substances to enhance stability, deliverability or solubility, such as buffering agents, tonicity adjusting agents, wetting agents, detergents and the like. Additives can also include additional active ingredients such as bactericidal agents, or stabilizers. For example, the solution can contain sodium acetate, sodium lactate, sodium chloride, potassium chloride, calcium chloride, sorbitan monolaurate or triethanolamine oleate. These compositions can be sterilized by conventional, well-known sterilization techniques, or can be sterile filtered. The resulting aqueous solutions can be packaged for use as is, or lyophilized, the lyophilized preparation being combined with a sterile aqueous solution prior to administration.

The VR1 agonists are often administered in specific formulations such as isobaric or hyperbaric solutions that may additionally contain other agents such as a long acting local anesthetic. The density of the solution can be controlled using methods known to those of skill in the art. For example, a solution can be made more hyperbaric by the addition of iohexol, iodixanol, metrizamide, sucrose, trehalose, glucose, or other biocompatible molecules with high specific gravity.

In some embodiments, the VR1 agonist is administered in conjunction with a local anesthetic. A local anesthetic refers to a drug that provides temporary numbness and pain relief in a specific region. Local anesthetics are well known to those of skill in the art. These includes, dibucaine, bupivacaine, ropivacaine, etidocaine, tetracaine, ropivicaine, procaine, chlorocaine, prilocaine, mepivacaine, lidocaine, xylocaine, 2-chloroprocaine, and acid addition salts or mixtures thereof.

The VR1 agonists can also be administered in conjunction with other agents. For example, the VR1 agonist can be administered with a dye or tracer compound when image-guided administration procedures are performed. Common agents include a radio-opaque dye or manetic resonance contrast agent such as gadlinium.

The VR1 agonists for use to selectively ablate VR1-expressing neurons are administered to a subject such as a mammal, preferably a primate or a human, but can also be used for other mammals such as horses, cows, sheep, pigs, dogs, cats, rabbits, or other animals.

5. Kits

After a pharmaceutical comprising a VR1 agonist for use in the methods of the invention has been formulated in a acceptable carrier, it can be placed in an appropriate container and labeled for treatment of an indicated condition, such as chronic pain. For administration of VR1 agonists, such labeling would include, e.g., instructions concerning the amount, frequency and method of administration. In one embodiment, the invention provides for a kit for the treatment of chronic pain in a human which includes a the VR1 agonist and instructional material teaching the indications, dosage and schedule of administration of the agonist. Often, such kits also include a local anesthetic.

It is understood that the examples and embodiments described herein are for illustrative purposes only and that various modifications or changes in light thereof will be suggested to persons skilled in the art and are to be included within the spirit and purview of this application and scope of the appended claims.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill in the art will readily recognize a variety of noncritical parameters that could be changed or modified to yield essentially similar results.

Example 1

Administration of VR-1 Agonist to Cells Expressing VR-1

The effect of VR-1 agonist administration to cells expression VR-1 was measured using the following methodology.

A VR1 expression vector encoding a VR-1/Green Fluorescent Protein construct was expressed in Cos7 and HEK293 cells using transient transfection. Western blot analysis showed that VR1 eGFP protein exhibited GFP-specific immunoreactivity and was not cleaved. The cells in the population that fluoresced green were voltage clamped and the holding potential adjusted to −60 mV. The first application of 10 µM capsaicin (CAP) to the cells induced a large inward current (N=5). Multiple exposures resulted in a gradual decrease, indicating receptor desensitization. The VR1 eGFP-mediated current was attenuated by co-incubation of an antagonist, 10 µM capsazepine (CPZ). Current versus voltage relationships demonstrated that the VR1eGFP-mediated current was not voltage sensitive. The reversal potential was calculated to be 78.3 mV, suggesting mixed cation selectivity for the channel.

Resiniferatoxin (RTX), in much lower concentration, induced a current similar to that of CAP; however, a single application of 125 pM RTX (N=12 cells) resulted in complete desensitization. Coincidentally, the membrane capacitance of VR1eGFP-transfected cells dropped dramatically (6±2.5 pF), indicating an about 600 µm$^2$ loss of plasma membrane due to RTX treatment. This calculation assumes a capacitance of 1 µF/cm$^2$ of membrane. However, the time constant remained the same.

The capacitance changes suggests either shedding or internalization of VR1eGFP membranes (Zimmerberg et al. *Proc. Natl. Acad. Sci. USA* 84: 1585-1589, 1987). To verify that the decrease in capacitance was mediated by VR1eGFP, the initial slope of the current evoked by RTX was plotted versus the change in capacitance for each cell. The slope of the evoked current correlated with the change in capacitance. In non-transfected cells, RTX neither evoked currents nor induced a change in capacitance. In accordance with the electrophysiological data, exposure to RTX induced Ca$^{2+}$ uptake in VR1eGFP-expressing HEK293 and Cos7 cells. This demonstrated that VR1eGFP can mediate ligand-induced Ca$^{2+}$-influx. RTX induced Ca$^{2+}$ uptake with an ED$_{50}$=0.1±0.05 nM (N=3) while capsaicin induced Ca$^{2+}$ uptake with an ED$_{50}$=0.5=±0.15 µM.

A VR1-tagged with a 12 amino acid ε-epitope was also tested in an NIH3T3 cell line expressing "VR1ε", a C-terminal epsilon epitope-tagged vanilloid 1 receptor.

Preparation of the plasmid vector expressing C-terminally epsilon epitope tagged vanilloid receptor was performed as follows. Plasmid expressing the rat vanilloid receptor (VR1) extended with the short, 12 amino acid ε-tag (KGFSYF-GEDLMP) C-terminally was constructed in a vector driven by the metallothionine (pMTH) promoter. The backbone vector has been previously described (Olah et al., *Anal Biochem* 221:94-102; 1994). Briefly, Sal I and Mlu I restriction endonuclease sites were incorporated into a VR1 PCR fragment. After digestion of the PCR fragment with these enzymes, the size-separated cDNA insert was ligated in the pεMTH plasmid vector at the compatible Xho I and Mlu I sites (Olah et al., 1994). The chimeric constructs were verified by sequencing and transiently transfected into NIH 3T3 cells employing the protocol provided for the lipofectamine reagent (Life Sciences, Gaithersburg, Md.).

Preparation of VR1ε expressing cell line—To prepare cell lines permanently expressing the recombinant VR1 with the C-terminal ε-tag NIH 3T3 cells were transiently transfected with the pMTH-VR1ε plasmid. GenePorter (GP) purchased from Gene Therapy Systems was used as transfection reagent. NIH 3T3 cells were seeded in 24 well plates a day before transfection, then 2 μg pMTH-VR1ε plasmid DNA/well was used together with 25 and 10 μl of GP reagent, respectively. The DNA and the GP were mixed in serum free Opti-MEM for 15 minutes at room temperature then placed on the cultured cells. After 3 hrs at 34° C. the incubation medium was supplemented with equal volume of complete DMEM containing 10% FBS, 1% streptomycin, and 1% glutamine. To prevent acidification of the culture medium the pH was buffered to 7.5 with 20 mM HEPES. To diminish heat induced activation of VR1, cells were cultured in incubator adjusted to 34° C. After 24 hrs cells were transferred into selection medium prepared in complete DMEM buffered with 20 mM HEPES to pH=7.5, containing 0.8 μg/ml geneticin (G418). The selection medium was changed every second days. After one month G418 resistant colonies were tested with vanilloid-induced $Ca^{2+}$-transport assays. A colony (A5) exhibiting RTX-induced $^{45}Ca^{2+}$-uptake >50 fold above the base line determined with non-transfected NIH3T3 cells was chosen for further studies.

Similar results were obtained for the VR1 tagged with the 12 amino acid ε-epitope, compared to the VR1 eGFP, indicating that a C-terminal tag per se, does not significantly change the calcium uptake parameters.

Assessment of the quantitative characteristic of $[^3H]RTX$ binding to eGFP- and e-tagged VR1 expressed in Cos7 cells showed that progressive $[^3H]RTX$ was almost completely inhibited by co-incubation with 10 uMCPZ. Both tagged recombinants exhibited a high affinity, dose-dependent interaction and cooperativity among the receptors. No significant $[^3H]RTX$ binding was detect in cells transfected with the eGFP plasmid alone.

Confocal microscopy showed that VR1eGFP was prominently found in the ER and to a lesser degree, in the plasma membrane. The physiological evidence, however, demonstrated the presence of functional receptor protein in the plasma membrane. Incubation of VR1eGFP-expressing cells with 1 nM RTX for 20 sec induced a dramatic fragmentation of the ER, appearance of microvilli at the plasma membrane, and rounding up of filamentous mitochondria. Although mitochondria reacted rapidly to 1 nM RTX or 1 uM CAP, no mixing between the VR1eGFP vesicles and the mitochondrial membranes was observed. Without external $Ca^{2+}$, the vanilloid-induced membrane alterations were delayed 5-10 min (vs. msec) in VR1eGFP-expressing cells. In cells expressing only eGFP, the mitochondria and ER did not change in response to vanilloid treatment.

Both electrophysiology and fluorescent microscopy demonstrated dramatic membrane remodeling in response to vanilloids in cells expressing VR1eGFP. VR1eGFP and VR1ε expression in transiently transfected cells conferred vanilloid-induced plasma membrane $^{45}Ca^{2+}$ flux. The effect of RTX on the cytosolic $Ca^{2+}$ was then examined by microfluorometry in transfected cells loaded with the $Ca^{2+}$ monitoring dye, Fura-2 AM. The resting $[Ca^{2+}]_i$ was similar in Cos 7 cells transfect with either VR1eGFP or eGFP plasmid. Addition of 1 nM RTX induced a rapid (within 10 sec) elevation of $[Ca^{2+}]_i$ in VR1eGFP-expressing cells that peaked at 500 nM at about 1 min and, consistent with the ER and mitochondrial damage, did not return to resting levels. In the absence of external $Ca^{2+}$, vanilloids were less effective. Cells expressing eGFP only showed no increase in $[Ca^{2+}]_i$.

Time lapse confocal microscopy demonstrated the in vivo dynamics of vanilloid action on live VR1eGFP-expressing cells. Prior to RTX treatment, VR1eGFP-decorated ER showed a similar morphology. Within 30 seconds of RTX treatment, the ER condensed and the nuclear envelope was outlined by the VR1eGFP fluorescence. These changes coincided with the increase in [Ca2+]i. VR1eGFP-expressing cells were visualized with 1 second scans at 1 minute intervals for one hour using confocal microscopy. Three minutes after addition of 1 nM RTX, the cells showed extensive accumulation of VR1eGFP at the nuclear membrane and in membrane vesicles around the nucleus, similar to that observed at 90 seconds. With time, progressively growing blebs were noted in the nuclear membrane. Cells showed membrane degradation concluding with bursting of the plasma membrane within an hour, often at about 45 minutes. Lower doses of RTX ($\leq 0.1$ nM) evoked slower nuclear membrane fragmentation.

This example demonstrates that application of VR1 antagonist to VR1-expressing cells triggers a cascade of events leading to cell death. These data showed that VR1 activation produces a transmembrane calcium flux which fragments the ER and mitochondria, causes propidium iodide uptake.

Example 2

VR1 Agonist Injection into the Trigeminal Ganglion

Methods

Trigeminal microinjections: Male Sprague Dawley rats (300 g) were anesthetized with a combination of ketamine/xylazine and placed in a stereotaxic frame. A 26 gauge stainless steel catheter, sharpened with a bevel of ~0.5 mm, was positioned at 2.5 mm posterior and 1.5 mm lateral to bregma. The needle was advanced till it touched the base of the skull. At this point the tip has penetrated through the trigeminal ganglion, which is ~1.2 mm in depth. The needle was retracted 0.5 mm and RTX (200 ng) was injected in a volume of 2 microliters over 1.5 to 2 min. The RTX was diluted with 0.9% saline from a stock solution which contained 1 mg/ml of RTX, 10% ethanol, 10% Tween 80 and 80% normal saline. The vehicle that was injected was a 1:10 dilution of the RTX stock vehicle using 0.9% saline as the diluent. The needle is left in place for an additional minute, withdrawn, and the scalp incision is closed with stainless steel clips.

Behavioral/physiological assessments: Nociceptive behavior was assessed by the capsaicin eye-wipe test. In this test a 0.01% solution of capsaicin is instilled into the eye. This causes the rat to squint, blink and wipe the eye with the forepaw. At the concentration used the wiping behavior lasts approximately one minute and the quantitative end point is the total number of wipes in one minute. Loss of nociceptive primary afferents also affects peripheral inflammation. This can be assessed by measuring peripheral plasma extravasation using intravenous administration of Evans blue dye during inflammation or activation of primary afferent endings by capsaicin. In the presence of nociceptive nerves topical capsaicin activates the primary afferent nerve ending and releases transmitters, these dilate the blood vessels and allow plasma proteins to extravasate into the tissue. Evans blue binds strongly to albumin and the skin turns blue due to the leakage of the blue albumin into the skin. There was a dramatic blockade of plasma extravasation by intraganglionic RTX.

Anatomical assessments: Rats were perfused with 4% paraformaldehyde via an intracardiac puncture and aortic cannulation. The ganglion and the brain stem/spinal cord region centered on the obex were removed. Tissues were stained for CGRP and Substance P, both peptides are made by primary afferent neurons that co-express the VR1 receptor. The nociceptive inputs from one ganglion are lateralized and project only to one side of the trigeminal nucleus caudalis. Thus, one side can be compared to the other in the same animal.

Results: In the eye wipe test, the unilateral control showed 20±2 wipes in the first minute. Treatment with 0.2 ug of RTX injected into the trigeminal ganglion resulted in no eye wipes within the first minutes (n=8 rats). In animals receiving 0.02 ug of RTX (n=4), the control values were 28±2 wipes in the first minute. RTX treatment resulted in a decrease in the number of wipes to 7±3 in the first minute. Control animals (n=10) receiving an injection of the vehicle alone showed 24 wipes in the first minute on the unaffected side compared to 23 wipes in the first minute on the injected side.

Staining of the ganglion for CGRP demonstrate that cells in the ganglion that received the RTX were killed by direct injection. RTX selectively removes C-fiber neurons from the ganglion. See FIGS. 1 and 2 where some of the large neurons remain intact after RTX injection. Their cell bodies are lightly toned rather than dark black. The loss of plasma extravasation on the ganglion-injected side of the rat's head showed that loss of cells in the ganglion is manifested by a corresponding loss of pain-sensing nerves in the skin.

The experiments demonstrated that direct administration of a vanilloid receptor agonist to the trigeminal ganglion results in killing of VR-1-expressing cells and a concordant decrease in sensitivity to pain.

Example 3

Intrathecal Administration of RTX

Pain sensitivity following intrathecal administration of RTX to rats was measured using a test for thermal sensitivity well known to those in the art, the paw withdrawal latency test (e.g., Hargreaves (1988) Pain 32:77-88). Sprague Dawley rats received 6 ug of RTX in a 5 microliter volume administered by lumbar puncture. The baseline sensitivity was 8.4±1.3 second. Following administration of RTX, the paw withdrawal latency was 18±1.2 seconds. No attenuation of mechanical pinch sensitivity was observed. Thus, RTX administration resulted in attenuation of thermal sensitivity.

Example 4

Administration of a VR1 Agonist to a Patient Suffering from Chronic Pain

Selective ablation of VR1-expressing neurons is often used to treat patients suffering from chronic pain. For example, the method can be used to treat a patient with chronic pain resulting from injury to a single nerve. In this example, because the injury is to a single nerve, one dorsal root ganglion is treated. The ganglion is visualized, often by CAT scan or fluoroscopy. Prior to injection of the VR1 agonist, e.g., RTX, a local anesthetic is administered. The RTX (for example, 400 ng) is administered in a volume of, e.g., 100 ul as a single injection directly into the dorsal root ganglion over one minute. Following administration the needle is removed and the patient undergoes observation. Administration of RTX results in the reduction of the symptoms of chronic pain the treated patient.

All publications and patent applications cited in this specification are herein incorporated by reference as if each individual publication or patent application were specifically and individually indicated to be incorporated by reference.

What is claimed is:

1. A method of treating chronic pain in a patient suffering from chronic pain; said method comprising administering resiniferatoxin intrathecally to the patient suffering from chronic pain, wherein the resiniferatoxin is administered as a single administration in an amount from about 100 nanograms to about 500 micrograms.

2. The method of claim 1, wherein the amount of resiniferatoxin is from about 500 nanograms to about 500 micrograms.

3. The method of claim 1, further comprising administering a local anesthetic to the patient.

4. The method of claim 3, wherein the local anesthetic is lidocaine, tetracaine, ropivicaine, or bupivacaine.

5. The method of claim 1, wherein the patient is a human.

6. The method of claim 1, wherein the patient is a dog, horse, cat, cow, sheep, pig, or rabbit.

7. The method of claim 1, wherein the chronic pain is pain associated with cancer.

8. The method of claim 1, wherein the resiniferatoxin is administered as a single bolus.

9. The method of claim 1, wherein the resiniferatoxin is infused over a period of time.

10. The method of claim 9, wherein the period of time is from about 1 to 5 minutes.

11. The method of claim 2, wherein the amount of resiniferatoxin is from about 500 nanograms to about 50 micrograms.

12. The method of claim 6, wherein the patient is a dog.

13. A method of treating chronic pain in a cancer patient suffering from chronic pain; said method comprising administering resiniferatoxin intrathecally to the cancer patient suffering from chronic pain, wherein the resiniferatoxin is administered as a single administration in an amount from about 100 nanograms to about 500 micrograms.

14. The method of claim 13, wherein the patient is a human.

* * * * *